(12) United States Patent
Baxter et al.

(10) Patent No.: US 6,426,356 B1
(45) Date of Patent: Jul. 30, 2002

(54) IMIDAZOETHYL THIOPHENES

(75) Inventors: Ellen W. Baxter, Glenside; Michele C. Jetter, Norristown, both of PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/440,869

(22) Filed: Nov. 16, 1999

Related U.S. Application Data

(60) Provisional application No. 60/108,934, filed on Nov. 18, 1998.

(51) Int. Cl.[7] .................. C07D 409/06; C07D 417/06; A61K 31/4178
(52) U.S. Cl. .................. 514/365; 514/397; 514/311.4; 514/315.1; 548/205
(58) Field of Search ............................ 548/205, 311.4, 548/315.1; 514/365, 397

(56) References Cited

U.S. PATENT DOCUMENTS

| | | | |
|---|---|---|---|
| 3,574,844 A | 4/1971 | Gardocki et al. | 424/272 |
| 4,914,207 A | 4/1990 | Nagel et al. | 546/167 |
| 5,621,113 A | 4/1997 | Boyd et al. | 548/315.1 |
| 5,750,720 A | 5/1998 | Boyd et al. | 548/315.1 |

FOREIGN PATENT DOCUMENTS

| | | |
|---|---|---|
| JP | 1-242571 | 9/1989 |
| WO | 92/14453 | 9/1992 |

OTHER PUBLICATIONS

Drug Dev. Res. 1995, 35,237.
Drug Dev. Res. 1995, 35,246.
J.Med. Chem. 1995, 38 (23),4615.
J. Med Chem. 1997, 40 (7), 1049.
Exp. Opin. Invest. Drugs 1995, 4(10),945.
Bioorg. Med. Chem Lett. 1995,5,2287.

Primary Examiner—Robert Gerstl
(74) Attorney, Agent, or Firm—John W. Harbour

(57) ABSTRACT

Certain imidazoethyl thiophenes/thiazoles and benzothiophenes of the formula:

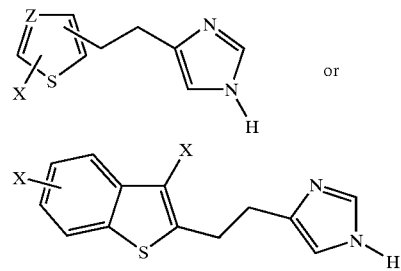

where

Z is CH or N; and

X is independently selected from the group consisting of hydrogen, $C_{1-4}$alkyl, bromine, chlorine, iodide, trifluoromethyl, $C_{4-1}$alkoxy and nitro; are $\alpha_2$-adrenoceptor agonists/antagonists which are useful in the treatment of hypertension, glaucoma, sexual dysfunction, depression, attention deficit hyperactivity disorder, the need for anesthesia, cardiac arrythmia or the need for analgesia.

7 Claims, No Drawings

IMIDAZOETHYL THIOPHENES

This application claims the benefit of provisional application 60/108,934 filed Nov. 18, 1998.

The present invention relates to compounds which bind to the $\alpha_2$-adrenoceptor. More particularly, the present invention relates to certain imidazoethyl thiophenes/thiazoles or benzothiophenes and analogues which are $\alpha_2$-adrenoceptor modulators.

BACKGROUND OF THE INVENTION $\alpha_2$-adrenoceptor modulators are useful to treat a variety of conditions, including, hypertension, glaucoma, sexual dysfunction, depression, attention deficit hyperactivity disorder, the need for anesthesia, cardiac arrythmia and the need for analgesia. Particularly, $\alpha_2$-adrenoceptor agonists are well known analgesics. $\alpha_2$-adrenoceptor antagonists have potential as antidepressants in their own right or as adjunct therapies to traditional inhibitors of monoamine reuptake.

Clonidine is a centrally acting $\alpha_2$-adrenoceptor agonist with wide clinical utility as an antihypertensive agent. Clonidine is believed to act by inhibiting the release of norepinephrine from sympathetic nerve terminals via a negative feedback mechanism involving $\alpha_2$-adrenoceptors located on the presynaptic nerve terminal. This action is believed to occur in both the central (CNS) and peripheral (PNS) nervous systems. More recently, the role of $\alpha_2$-adrenoceptor agonists as analgesic agents in humans and antinociceptive agents in animals has been demonstrated. Clonidine and other $\alpha_2$-adrenoceptor agonists have been shown to produce analgesia through a non-opiate mechanism and, thus, without opiate liability. However, other behavioral and physiological effects were also produced, including sedation and cardiovascular effects.

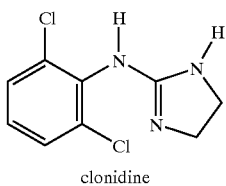

clonidine

Medetomidine, detomidine, and dexmedetomidine are $\alpha_2$-adrenoceptor agonists. Dexmedetomidine is used clinically in veterinary medicine as a sedatives/hypnotic for pre-anaesthesia. These compounds are hypotensive in animals and in humans, but the magnitude of this cardiovascular effect is relatively insignificant.

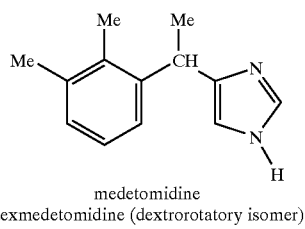

medetomidine
dexmedetomidine (dextrorotatory isomer)

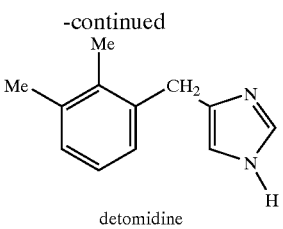

detomidine

U.S. Pat. No. 3,574,844, Gardocki et al., teach 4-[4 (or 5)-imidazolylmethyl]-oxazoles as effective analgesics. The disclosed compounds are of the general formula:

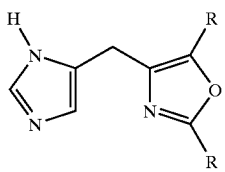

Compounds of this type are insufficiently active and suffer from unwanted side effects.

U.S. Pat. No. 4,913,207, Nagel et al., teach arylthiazolylimidazoles as effective analgesics. The disclosed compounds are of the general formula:

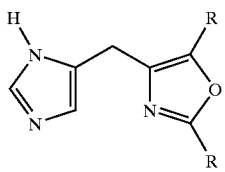

Compounds of this type are insufficiently active and suffer from unwanted side effects.

WO92/14453, Campbell et al., teach 4-[(aryl or heteroaryl)methyl]-imidazoles as effective analgesics. The disclosed compounds are of the general formula:

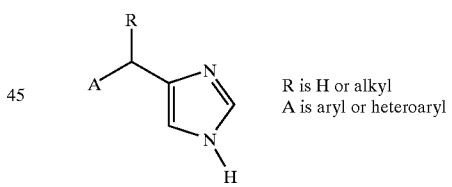

R is H or alkyl
A is aryl or heteroaryl

The disclosed compounds are insufficiently active and suffer from unwanted side effects.

Kokai No. 1-242571, Kihara et al., disclose a method to produce imidazole derivatives for use, among other uses, as antihypertensive agents.

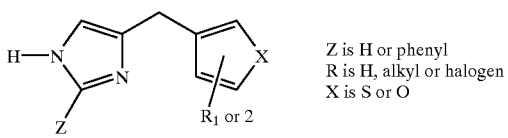

Z is H or phenyl
R is H, alkyl or halogen
X is S or O

A single mixture of compounds meeting the above formula was reportedly produced by the inventive method. This was a mixture of 4-(2-thienyl)-methylimidazole and 4-(3-thienyl)-methylimidazole represented by the following formula:

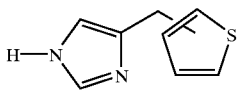

The disclosed compounds are insufficiently active and suffer from unwanted side effects.

U.S. Pat No. 5,621,113 and U.S. Pat No. 5,750,720, Boyd and Rasmussen disclose substituted 2 and 3-thienyl methylimidazoles as effective analgesic agents.

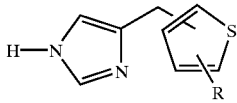

Many potent and selective $\alpha_2$ antagonists, such as idazoxan, have been synthesized and evaluated in limited clinical trials as antidepressants. (*J. Med. Chem.* 1995, 38 (23), 4615.). Mirtazapine is a closely related analog of the established antidepressant mianserin. This compound has been shown to be an antagonist at $\alpha_2$ receptors snd exhibits antidepressant activity in vivo. (*Exp. Opin. Invest. Drugs* 1995, 4 (10), 945.). An agent with the dual profile of a 5 HT reuptake inhibitor and an a2 antagonist might serve to enhance synaptic concentrations of 5-HT relative to that achievable through 5-HT uptake inhibition alone and in turn produce a more effective antidepressant response. A novel series of compounds with such a profile was found to possess putative antidepressant effects in vivo (*J. Med. Chem.* 1997, 40 (7), 1049; *Bioorg. Med. Chem Lett.* 1995, 5, 2287.; *Drug. Dev. Res.* 1995, 35, 237.; *Drug. Dev. Res.* 1995, 35, 246.)

SUMMARY OF THE INVENTION

Briefly, there is provided by the present invention compounds which are $\alpha_2$-adrenoceptor modulators of the formula:

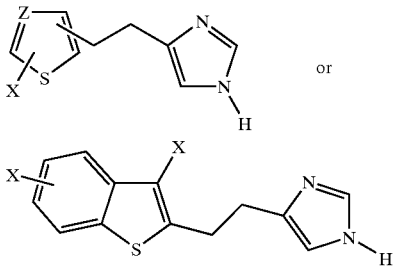

where

Z is CH or N; and

X is independently selected from the group consisting of hydrogen, $C_{1-4}$alkyl, bromine, chlorine, iodide, trifluoromethyl, $C_{1-4}$alkoxy and nitro.

DETAILED DESCRIPTION OF THE INVENTION

The compounds of the present invention are prepared by the methods shown in Scheme 1. Scheme 1 is drawn to depict only thiophene, but the thiophene of this scheme could in each instance be replaced with the equivalent benzothiophene to produce the benzothiophene end product. In Scheme 1, an appropriately substituted thiophene aldehyde A1 is reduced with an appropriate reducing agent such as $NaBH_4$ in a solvent such as methanol to give the thiophene alcohol A2. This thiophene alcohol A2 is converted to the thiophene bromide A3 by reaction with $CBr_4$/$PPh_3$. This bromomethyl thiophene A3 is then reacted with $PPh_3$ in a solvent such as THF to yield the thiophene phosphonium salt A4. This phosphonium salt undergoes Wittig reaction with $N^1$-trityl-imidazole-4-carboxaldehyde in the presence of an appropriate base such as sodium methoxide in methanol or lithium hexamethyldisilazide in THF. The resultant mixture of cis and trans isomers A5 are deprotected under acidic conditions such as with acidic methanol or trifluoroacetic acid in dichloromethane. The desired product is then obtained by catalytic reduction to yield the appropriately substituted imidazoethyl thiophenes A6.

SCHEME 1

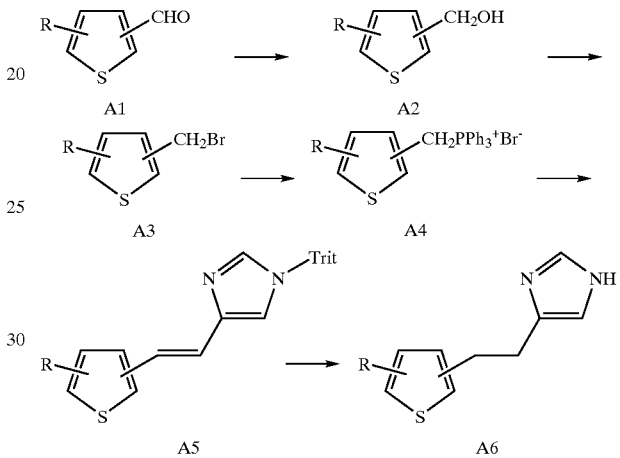

Alternatively, the phosphonium salt of the thiophene A4 can be obtained by direct reaction of the appropriately substituted hydroxymethylthiophene A2 with triphenylphosphine hydrobromide in trichloromethane as illustrated in Scheme 2.

SCHEME 2

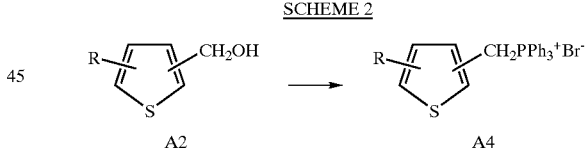

The thiazoles can be made according to the procedure of Scheme 1 from an equivalent thiazole phosphonium salt A4 to an equivalent imidazoethylthiazole A6. To obtain the equivalent thiazole phosphonium salt A4 the procedure disclosed by Williams and Brooks *Tetrahedron Letters* 1996, 983 should be employed. In the case where R is hydrogen, $C_{1-4}$alkyl, $C_{1-4}$alkoxy and trifluoromethyl, the appropriately substituted thiophene alkenyl imidazole A5 may be produced and the substituent in question will stably endure the reactions of Scheme 1 or Scheme 2 to arrive at target products A6. In the case where R is chlorine, bromine and nitro, the saturated product A6 may be obtained from the unsaturated intermediate A5 by alternate reduction conditions such as borane/methylsulfide or triethylsilane/trifluoroacetic acid.

The compounds of the present invention may be used to treat a medical condition as named herein, such as, mild to moderate pain in warm-blooded animals, such as, humans by administration of an effective dose. The dosage range would be from about 10 to 3000 mg, in particular about 25 to 1000 mg or about 100 to 500 mg, of active ingredient 1 to 4 times per day for an average (70 kg) human although it is apparent that activity of individual compounds of the invention will vary as will the pain being treated. In regard to the use of these $\alpha_2$-adrenoceptor modulators to treat hypertension, glaucoma, sexual dysfunction, depression, attention deficit hyperactivity disorder, the need for anesthesia and cardiac arrythmia, a therapeutically effective dose can be determined by persons skilled in the art by use of established animal models. Pharmaceutical compositions of the invention comprise the formula (I) compounds as defined above, particularly in admixture with a pharmaceutically-acceptable carrier.

To prepare the pharmaceutical compositions of this invention, one or more compounds of the invention or salt thereof as the active ingredient, is intimately admixed with a pharmaceutical carrier according to conventional pharmaceutical compounding techniques, which carrier may take a wide variety of forms depending on the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above.

The pharmaceutically acceptable salts referred to above generally take a form in which the imidazolyl ring is protonated with an inorganic or organic acid. Representative organic or inorganic acids include hydrochloric, hydrobromic, hydroiodic, perchloric, sulfuric, nitric, phosphoric, acetic, propionic, glycolic, lactic, succinic, maleic, famaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic or saccharic.

Biological Procedures

The activity of compounds of the invention as $\alpha_2$ modulators may be demonstrated by the in vivo and in vitro assays as described below:

Alpha-2D Adrenergic Receptor Binding Assay

Male, Wistar rats (150–250 g, VAF, Charles River, Kingston, N.Y.) are sacrificed by cervical dislocation and their brains removed and placed immediately in ice cold HEPES buffered sucrose. The cortex is dissected out and homogenized in 20 volumes of HEPES sucrose in a Teflon™-glass homogenizer. The homogenate is centrifuged at 1000 g for 10 min, and the resulting supernatant centrifuged at 42,000 g for 10 min. The resulting pellet is resuspended in 30 volumes of 3 mM potassium phosphate buffer, pH 7.5, preincubated at 25 ° C. for 30 min and recentrifuged. The resulting pellet is resuspended as described above and used for the receptor binding assay. Incubation is performed in test tubes containing phosphate buffer, 2.5 mM $MgCl_2$, aliquots of the synaptic membrane fraction, the ligand $^3$H-para-aminoclonidine and test drug at 25° C. for 20 min. The incubation is terminated by filtration of the tube contents through glass fiber filter sheets. Following washing of the sheets with 10 mM HEPES buffer, the adhering radioactivity is quantified by liquid scintillation spectrometry.

Binding of the test drug to the receptor is determined by comparing the amount of radiolabeled ligand bound in control tubes without drug to the amount of radiolabeled ligand bound in the presence of the drug. Dose-response data are analyzed with LIGAND, a nonlinear curve fitting program designed specifically for the analysis of ligand binding data. This assay is described by Simmons, R. M. A., and Jones, D. J., Binding of [$^3$H-]prazosin and [$^3$H-]p-aminoclonidine to ($\alpha$-Adrenoceptors in Rat Spinal Cord, *Brain Research* 445:338–349, 1988.

Mouse Acetylcholine Bromide-Induced Abdominal Constriction Assay (MAIT)

The mouse acetylcholine bromide-induced abdominal constriction assay, as described by Collier et al. in Brit. J. Pharmacol. Chem. Ther., 32: 295–310, 1968, with minor modifications was used to assess analgesic potency of the compounds herein. The test drugs or appropriate vehicle were administered orally (p.o.) and 30 minutes later the animal received an intraperitoneal (i.p.) injection of 5.5 mg/kg acetylcholine bromide (Matheson, Coleman and Bell, East Rutherford, N.J.). The mice were then placed in groups of three into glass bell jars and observed for a ten minute observation period for the occurrence of an abdominal constriction response (defined as a wave of constriction and elongation passing caudally along the abdominal wall, accompanied by a twisting of the trunk and followed by extension of the hind limbs). The percent inhibition of this response to a nociceptive stimulus (equated to % analgesia) was calculated as follows: The % Inhibition of response, i.e., % analgesia is equal to the difference between the number of control animals responding and the number of drug-treated animals responding times 100 divided by the number of control animals responding.

At least 15 animals were used for control and in each of the drug treated groups. At least three doses were used to determine each dose response curve and $ED_{50}$ (that dose which would produce 50% analgesia). The $ED_{50}$ values and their 95% fiducial limits were determined by a computer assisted probit analysis.

Biological Data

Tables 1–3 list compounds made in the examples below with certain biological and physical data.

TABLE 1

| Cpd# | 2 or 3 thienyl | X | R' | $\alpha_{2D}K_i$ (nM) | MAIT | Mass (calc) | Mass (obs) |
|---|---|---|---|---|---|---|---|
| Cp-1 | Thien-2-yl | 3-Me | H | 0.075 | 93 po | 192.29 | 193 |
| Cp-2 | Thien-2-yl | H | H | 0.1 | 60 po | 178.26 | 179 |
| Cp-3 | Thien-3-yl | H | H | 0.53 | 53 po | 178.26 | 179 |
| Cp-4 | Thien-2-yl | 5-Me | H | 1.1 | 7 po | 192.29 | 193 |
| Cp-5 | Thien-3-yl | 2-Et | H | 1.8 | 67 po | 206.31 | 207 |
| Cp-6 | Thien-2-yl | 5-Et | H | 1.2 | 20 po | 206.31 | 207 |
| Cp-7 | Thien-2-yl | 3-Me | Me | ND | 20 po | 206.31 | 207 |
| Cp-8 | Thien-2-yl | 4-Et | H | 0.15 | 20 po | 206.31 | 207 |

TABLE 2

| Cpd# | X | $\alpha_{2D}K_i$ (nM) | MAIT | Mass (calc) | Mass (obs) |
|---|---|---|---|---|---|
| Cp-9 | 3-Me | 14 | 7 sc | 242.35 | 243 |
| Cp-10 | H | 31 | 20 sc | 228.32 | 229 |

TABLE 3

| Cpd# | 2 or 3 thienyl | X | R | $\alpha_{2D}K_i$ (nM) | MAIT | Mass (calc) | Mass (obs) |
|---|---|---|---|---|---|---|---|
| Cp-11 | Thien-2-yl | H | H | ND | 33 po | 176.24 | 177 |
| Cp-12 | Thien-2-yl | 5-Me | H | 22 | 7 po | 190.27 | 191 |
| Cp-13 | Thien-2-yl | 3-Me | H | 3.2 | ND | 190.27 | 191 |
| Cp-14 | Thien-2-yl | 5-Cl | H | 17 | 20 po | 210.69 | 212 |
| Cp-15 | Thien-3-yl | H | H | 9.4 | 13 sc | 176.24 | 177 |
| Cp-16 | Thien-2-yl | 4-Br | H | 31 | 20 po | 255.14 | 255 |
| Cp-17 | Thien-2-yl | 5-Et | H | 22 | 13 sc | 204.30 | 205 |
| Cp-18 | Thien-2-yl | 4-Et | H | 26 | 53 sc | 204.30 | 205 |
| Cp-19 | Thien-3-yl | 2-Et | H | ND | ND | 204.3 | 205 |
| Cp-20 | Thien-2-yl | 3-Me | Me | ND | ND | 204.3 | 205 |

TABLE 4

| Cpd# | $\alpha_{2D}K_i$ (nM) | MAIT | Mass (calc) | Mass (obs) |
|---|---|---|---|---|
| Cp-21 | 4 | 13 po | 193.3 | 194 |

The following Examples illustrate the invention:

EXAMPLE 1

Cp-1 and Cp-13

3-Methyl-thiophene-2-carboxaldehyde (0.04 moles) was dissolved in 50 ml of methanol and cooled to 0 C in an ice-bath. Sodium borohydride (0.02 moles) was added and the reaction mixture was stirred for 1.5 hours at which point TLC analysis (70:30 hexane/ethyl acetate) indicated the reaction was complete. Water (20 ml) was added to quench the reaction followed by the addition of 30 ml of $CH_2Cl_2$. The $CH_2$ $Cl_2$ layer was separated and dried over $NASO_4$. The solvent was evaporated under reduced pressure. The product was obtained as a pale yellow oil and used without further purification.

3-Methyl-2-hydroxymethyl thiophene (0.01 moles) was dissolved in 50 ml of $CH_2Cl_2$ and $CBr_4$ (0.01 moles) was added. The clear reaction mixture was stirred at room temperature for 10 minutes, then cooled to 0 C (ice bath). Triphenylphosphine (0.01 moles) was then added and the reaction mixture was stirred at room temperature for an additional 2 hours. Saturated $NaHCO_3$ (25 ml) was added to the reaction mixture and the $CH_2$ $Cl_2$ layer was separated. The organic layer was washed with brine (25 ml), dried over $Na_2SO_4$ and evaporated under reduced pressure. Cold $Et_2O$ (25 ml) was added to the residue to precipitate the triphenylphosphineoxide which was filtered off. The filtrate was evaporated under reduced pressure to yield the product as a brown oil. 3-Methyl-2-bromomethyl thiophene (0.03 moles) was dissolved in 100 ml of THF and $PPh_3$ (0.03 moles. 1.0 equivalents) was added. The reaction mixture was heated at reflux for 1 hour or until TLC (70:30 Hexane/EtOAc) showed the disappearance of starting material. The reaction mixture was cooled and the precipitated solid was collected by filtration. The product (off-white solid) was used in the next reaction without further purification.

$^1$H NMR ($CDCl_3$): δ 1.6 (d, 3 H, $CH_3$), 5.6 (d, 2H, $CH_2PPh_3$), 6.7 (d, 1H), 7.1 (m, 1H), 7.6–8.0 (m, 15H).

The phosphonium salt (0.004 moles) was dissolved in 20 ml of methanol and sodium methoxide in methanol was added (0.9 ml of a 0.5 M solution, 0.004 moles, 1.0 equivalent). To this solution was added $N^1$-tritylimidazole-4-carboxaldehyde (0.004 moles, 1.0 equivalent) and the reaction mixture was heated at reflux for 16 hours. The reaction mixture was cooled and the solvent was evaporated under reduced pressure. The residue was taken up in $CH_2Cl_2$, washed with brine, dried over $Na_2SO_4$ and evaporated under reduced pressure. The product was purified by chromatography on silica gel eluting with 60:40 hexane/ethyl acetate. The product was obtained as a pale yellow oil.

$^1$H NMR analysis showed the product to be a mixture of cis and trans isomers. After characterization by $^1$H NMR, these compounds were taken on for deprotection.

Alternatively, lithium hexamethyldisilazide (1.0M in THF) could be used as the base. In this case, the LiHMDS was added to a slurry of the phosphonium salt in 20 ml of THF at 0 C. The reaction mixture was stirred at 0 C for 30 minutes and then allowed to warm to room temperature. The reaction mixture was then stirred at room temperature for 16 hours. The solvent was evaporated under reduced pressure. $CH_2Cl_2$ (50 ml) was added to the residue and washed with $H_2O$ (20 ml). The organic layer was separated, dried over $Na_2SO_4$ and evaporated under reduced pressure. The residue was chromatographed on silica gel eluting with 70:30 hexane/ethyl acetate. The product was isolated as a pale yellow thick oil. $^1$H NMR analysis showed the product to be a mixture of cis and trans isomers.

Deprotection:

The product above (0.005 mole) was dissolved in 20 ml of methanol (did not dissolve completely) and 1.5 ml of concentrated HCl was added. The clear yellow solution was heated at reflux for 16 hours. The reaction mixture was cooled and the solvent was evaporated under reduced pressure. Methanol was added to the oily residue and evaporated 2 additional times. The residue was twice triturated with ether to remove the trityl byproduct. The solid was collected and then dissolved in 10 ml of $H_2O$. This solution was basified by the addition of solid $Na_2CO_3$ and extracted with 15 ml of ether. The ether layer was dried over $K_2CO_3$ and evaporated to a brownish oil. This oil was characterized by $_1$H NMR to be composed of predominantly the trans isomer. Cp-13 was obtained from this trans isomer free bases by adding 1M HCl in ether.

$^1$H NMR ($CD_3OD$): δ 2.35 (, s, 3H, $CH_3$), 6.7–6.8 (d, 1H, J=16.3, CH=CH), 6.9 (d,1H, J=5.1, thiophene), 7.3 (d, 1H, J=5.1, thiophene), 7.5–7.55 (d, 1H, J=16.3, CH=CH, 7.6 (s, 1H, imidazole H-5), 8.9 (s, 1H, imidazole H-2).

Reduction

The mixture of thiophene alkenyl imidazoles (0.004 mole) was dissolved in 20 ml of methanol. To this solution was added 250 mg of 10% Pd/C. The reaction mixture was hydrogenated at 45 si for 5 hours. The reaction mixture was filtered through Celite and the solvent was evaporated under reduced pressure. $CH_2Cl_2$ (10 ml) was added to the residue and evaporated.

1.0 M HCl in diethylether was added to the residue to form the hydrochloride salt, which is Cp-1. The product was obtained as a beige solid.

$^1$H NMR ($CD_3OD$): δ 2.1 (s, 3H, $CH_3$), 3.0 (t, 2H, J=7.0, $CH_2$ $CH_2$), 3.1 (t, 2H, J=7.0, $CH_2$ $CH_2$), 6.8 (d, 1H, J=5.0, thiophene), 7.1 (d, 1H, J=5.0), 7.2 (s, 1H-5), 8.8 (s, 1H, imidazole H-2).

Alternate Method for the Formation of the Phosphonium Salt

Triphenylphosphine hydrobromide (0.009 moles) was added to a solution of 3-methyl-2-hydroxymethyl thiophene (0.01 moles) dissolved in 20 ml of $CHCl_3$. The clear yellow reaction mixture was heated at reflux for 1 hour. The reaction mixture was then cooled to room temperature and the solvent was evaporated under reduced pressure. The residue was triturated with 20 ml of $Et_2O$. The off-white solid which formed was collected by filtration. This product was used in the next reaction without further purification.

EXAMPLE 2

Cp-2 and Cp-11

2-Hydroxymethyl thiophene (0.01 moles) was dissolved in 50 ml of $CH_2$ $Cl_2$ and $CBr_4$ (0.01 moles) was added. The clear reaction mixture was stirred at room temperature for 10 minutes, then cooled to 0 C (ice bath). Triphenylphosphine (0.01 moles) was then added and the reaction mixture was stirred at room temperature for an additional 2 hours. Saturated $NaHCO_3$ (25 ml) was added to the reaction mixture and the $CH_2$ $Cl_2$ layer was separated. The organic layer was washed with brine (25 ml), dried over Na2SO4 and evaporated under reduced pressure. Cold $Et_2O$ (25 ml) was added to the residue to precipitate the triphenylphosphineoxide which was filtered off. The filtrate was evaporated under reduced pressure to yield the product as a pale yellow oil.

**Caution: According to the literature, this compound is a powerful lachrymator and may explode without warning. Because of the instability of this compound, the filtrate was concentrated but not evaporated to dryness.

2-Bromomethyl thiophene (0.03 moles) was dissolved in 100 ml of THF and $PPh_3$ (0.03 moles. 1.0 equivalents) was added. The reaction mixture was heated at reflux for 1 hour or until TLC (70:30 Hexane/EtOAc) showed the disappearance of starting material. The reaction mixture was cooled and the precipitated solid was collected by filtration (9.88 g, 75% yield). This material was used in the next reaction without further purification.

$^1$H NMR ($CDCl_3$): δ 5.25 (d, 2H, $CH_2PPh_3$), 7.6–7.9 (m, 15 H)

The phosphonium salt (0.004 moles) was dissolved in 20 ml of methanol and sodium methoxide in methanol was added (0.9 ml of a 0.5 M solution, 0.004 moles, 1.0 equivalent). To this solution was added $N^1$-tritylimidazole-4-carboxaldehyde (0.004 moles, 1.0 equivalent) and the reaction mixture was heated at reflux for 16 hours. The reaction mixture was cooled and the solvent was evaporated under reduced pressure. The residue was taken up in $CH_2Cl_2$, washed with brine, dried over $Na_2SO_4$ and evaporated under reduced pressure. The product was purified by chromatography on silica gel eluting with 60:40 hexane/ethyl acetate. The product was obtained as a pale yellow oil (1.02 g, 61% yield). $^1$H NMR analysis showed the product to be a mixture of cis and trans isomers. After characterization by $^1$H NMR, these compounds were taken on for deprotection.

Alternatively, lithium hexamethyldisilazide (1.0M in THF) could be used as the base. In this case, the LiHMDS was added to a slurry of the phosphonium salt in 20 ml of THF at 0 C. The reaction mixture was stirred at 0 C for 30 minutes and then allowed to warm to room temperature. The reaction mixture was then stirred at room temperature for 16 hours. The solvent was evaporated under reduced pressure. $CH_2$ $Cl_2$ (50 ml) was added to the residue and washed with $H_2O$ (20 ml). The organic layer was separated, dried over $Na_2SO_4$ and evaporated under reduced pressure. The residue was chromatographed on silica gel eluting with 70:30 hexane/ethyl acetate. The product was isolated as a pale yellow thick oil. $^1$H NMR analysis showed the product to be a mixture of cis and trans isomers. A small amount of pure cis and trans product were obtained upon further chromatographic separation.

$^1$H NMR trans isomer ($CDCl_3$): δ 6.3–6.4 (d 1H, J=15.4), 6.5–6.6 (d, 1H, J=15.4 6.85 (m, 2H), 7.05 (s, 1H, imidazole H-5)), 7.0–7.4 (m, 17H), 7.45 (s, 1H, imidazol H-2)

Deprotection:

The product above (0.005 mole) was dissolved in 20 ml of methanol (did not dissolve completely) and 1.5 ml of concentrated HCl was added. The clear yellow solution was heated at reflux for 16 hours. The reaction mixture was cooled and the solvent was evaporated under reduced pressure. Methanol was added to the oily residue and evaporated 2 additional times. The residue was twice triturated with ether to remove the trityl byproduct. The oily product (HCl salt) was characterized by $^1$H NMR and found to be trans(as detected by $^1$H NMR), Cp-11.

$^1$H NMR (CD$_3$OD): δ 6.8–6.9 (d, 1H, J=15.2), 7.1 (m, 1H), 7.35–7.45 (d, 1H, J=7.6 (s, 1H, imidazole H-5), 8.9 (s, 1H, imidazole H-2).

Reduction

To a solution of the unsaturated hydrochloride salt (0.004 mole) in 20 ml of methanol was added 250 mg of 10% Pd/C. The reaction mixture was hydrogenated at 45 psi for 4 hours. The reaction mixture was filtered through Celite and the solvent was evaporated under reduced pressure. The residue was triturated with petroleum ether to yield the product as a grayish powder. This powder was recrystallized from acetone/petroleum ether to give the hydrochloride salt as tan crystals, Cp-2.

$^1$H NMR (CD$_3$OD): δ 3.1 (t, 2H, CH$_2$), 3.3 (t, 2H, CH$_2$), 6.8 (m, 1H), 6.9 (m, 1H), (m, 1H), 7.3 (s, 1H, imidazole, H-5), 8.85 (s, 1H, imidazole H-2).

Alternate Method for the Formation of the Phosphonium Salt

Triphenylphosphine hydrobromide (0.009 moles) was added to a solution of 2-hydroxymethyl thiophene (0.01 moles) dissolved in 20 ml of CHCl$_3$. The clear yellow reaction mixture was heated at reflux for 1 hour. The reaction mixture was then cooled to room temperature and the solvent was evaporated under reduced pressure. The residue was triturated with 20 ml of Et$_2$O. The white solid which formed was collected by filtration (3.73 g, 85% yield). This product was used in the next reaction without further purification.

EXAMPLE 3

Cp-12, Cp-14, Cp-15, Cp-16, Cp-17, Cp-18, Cp-19 and Cp-20 were synthesized analogously to Cp-11 and Cp-13. Cp-3, Cp-4, Cp-5, Cp-6, Cp-7 and Cp-8 were synthesized analogously to Cp-1 and Cp-2.

EXAMPLE 4

Cp-10

Thianaphthene (0.04 moles) was dissolved in 100 ml of dry THF. The clear solution was cooled to −78 C (dry ice/acetone) and stirred at −78 C for 10 minutes. To this solution was added n-butyl lithium (0.044 moles) via syringe and the reaction mixture was stirred at −78 C for 1 hour. N-formyl piperidine (0.04 mole) was then added and the reaction mixture was stirred at −78 C for an additional 1.5 hours. The clear pale yellow reaction mixture was allowed to warm to room temperature and stirred for 1 hour at which time TLC (70:30 hex/EtOAc) indicated the disappearance of starting material. Saturated NH$_4$ Cl (30 mL) was added to the reaction mixture and it was extracted with CH$_2$Cl$_2$ (2×50 ml). The organic layer was dried over Na$_2$SO$_4$ and evaporated under reduced pressure. The residue was chromatographed on silica gel eluting with 70:30 hexane/EtOAc. The product was obtained as yellow oil (75% yield).

$^1$H NMR (CDCl$_3$): δ 7.4 (m, 2H, aromatic, thiophene), 7.85–8.1 (m, 3H, aromatic), 10.1 (s, 1H, CHO)

Thianaphthene-2-carboxaldehyde (0.04 moles) was dissolved in 50 ml of methanol and cooled to 0 C in an ice-bath. Sodium borohydride (0.02 moles) was added and the reaction mixture was stirred for 1 hour at which point TLC analysis (70:30 hexane/ethyl acetate) indicated the reaction was complete. Water (20 ml) was added to quench the reaction followed by the addition of 30 ml of CH$_2$ Cl$_2$. The CH$_2$ Cl$_2$ layer was separated and dried over N$_2$SO$_4$. The solvent was evaporated under reduced pressure. The product was obtained as a pale yellow oil and used without further purification.

$^1$H NMR (CDCl$_3$): δ 1.9 (t, 1H, OH), 4.9 (d, 2H, CH$_2$OH), 7.2 (s, 1H, thiophene), 7.3 (m, 2H, aromatic), 7.7 (d, 1H, aromatic), 7.8 (d, 1H, aromatic).

2-Hydroxymethyl thianaphthene (0.01 moles) was dissolved in 50 ml of CH$_2$ Cl$_2$ and CBr$_4$ (0.01 moles) was added. The clear reaction mixture was stirred at room temperature for 10 minutes, then cooled to 0 C (ice bath). Triphenylphosphine (0.01 moles) was then added slowly and the reaction mixture was stirred at room temperature for an additional 2 hours. The clear colorless solution was now clear dark yellow-orange. A precipitate was evident which was filtered off. The filtrate was washed sequentially with saturated NaHCO$_3$ (25 mL) and H$_2$O (25 mL), dried over Na$_2$SO$_4$ and then evaporated under reduced pressure. Cold Et2O (25 ml) was added to the residue to precipitate the triphenylphosphineoxide which was filtered off. The filtrate was evaporated under reduced pressure to yield the product as a yellow-orange oil which was used without further purification in the next step.

2-Bromomethyl thianaphthene (0.006 moles) was dissolved in 20 ml of THF and PPh$_3$ (0.006 moles. 1.0 equivalents) was added. The reaction mixture was heated at reflux for 30 minutes or until-TLC (70:30 Hexane/EtOAc) showed the disappearance of starting material. The reaction mixture was cooled and the precipitated solid was collected by filtration. The product (yellow solid) was used in the next reaction without further purification. $^1$H NMR (CDCl$_3$): δ 5.9 (d, 2H, CH$_2$PPh$_3$), 7.2–7.3 (m 3H,), 7.5–7.8 (m, 17H).

The phosphonium salt (0.001 moles) was dissolved in 10 ml of methanol and sodium methoxide in methanol was added (2.8 ml of a 0.5 M solution, 0.0014 moles). To this solution was added N$^1$-tritylimidazole-4-carboxaldehyde (0.001 moles) and the reaction mixture was heated at reflux for 3 hours. The cloudy light yellow reaction mixture was cooled and filtered. The product was obtained as a pale yellow solid. $^1$H NMR analysis showed the product to be a mixture of cis and trans isomers. After characterization by $^1$H NMR, these compounds were taken on for deprotection.

Deprotection:

The product above (0.0005 mole) was dissolved in 10 ml of methanol (did not dissolve completely) and 0.5 ml of concentrated HCl was added. The clear yellow solution was heated at reflux for 16 hours. The reaction mixture was cooled and the solvent was evaporated under reduced pressure. Methanol was added to the oily residue and evaporated 2 additional times. The residue was twice triturated with ether to remove the trityl byproduct. The solid was collected and was characterized by $^1$H NMR to be a mixture of the cis and trans isomers.

Reduction:

The mixture of thiophene alkenyl imidazoles (0.004 mole) was dissolved in 20 ml of methanol. To this solution was added 250 mg of 10% Pd/C. The reaction mixture was hydrogenated at 35 psi for 4 hours. The reaction mixture was filtered through Celite and the solvent was evaporated under reduced pressure. CH$_2$Cl$_2$ (10 ml) was added to the residue and evaporated. 1.0 M HCl in diethylether was added to the residue to form the hydrochloride salt. The product was obtained as a yellow-brown solid and recrystallized from acetone to yield a yellow solid.

$^1$H NMR (CD$_3$OD): δ 3.1–3.2 (t, 2H, J=7.5, CH$_2$CH$_2$), 3.3–3.4 (t, 2H, J=7.5, CH$_2$CH$_2$), 7.1 (s, 1H, imidazole H-5), 7.2–7.4 (, 3H, aromatic), 7.6 (d, 1H, aromatic), 7.8 (d, 1H, aromatic), 8.8 (s, 1H, imidazole H-2).

EXAMPLE 5

Cp-9 was Synthesized Analogously to Cp-10

EXAMPLE 6

Cp-21 was synthesized by first making the thiazole phosphonium salt according to the procedure of Williams and Brooks *Tetrahedron Letters* 1996, 983. This phosphonium salt was treated in an analogous manner to the thiophene phosphonium salts in Examples 1 and 2.

What is claimed is:
1. The α$_2$-adrenoceptor agonist of the formula:

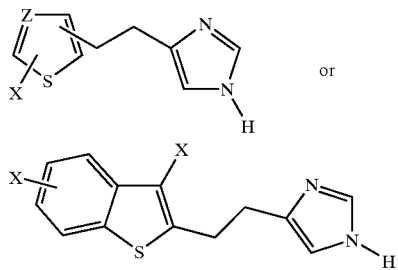

where

Z is CH or N; and

X is independently selected from the group consisting of hydrogen, C$_{1-4}$alkyl, bromine, chlorine, iodide, trifluoromethyl, C$_{1-4}$alkoxy and nitro.

2. The α$_2$-adrenoceptor agonist of the formula:

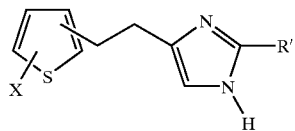

wherein the variables are dependently selected from the groups consisting of:

| 2 or 3 thienyl | X | R' |
|---|---|---|
| Thien-2-yl | 3-Me | H |
| Thien-2-yl | H | H |
| Thien-3-yl | H | H |
| Thien-2-yl | 5-Me | H |
| Thien-3-yl | 2-Et | H |
| Thien-2-yl | 5-Et | H |
| Thien-2-yl | 3-Me | Me |
| Thien-2-yl | 4-Et | H |

3. The compound of claim 1 having the general formula:

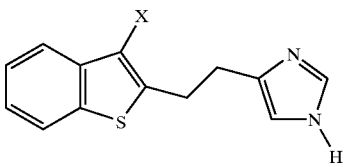

wherein the variables are dependently selected from the groups consisting of:

X

3-Me

H.

4. The α$_2$-adrenoceptor agonist of the formula:

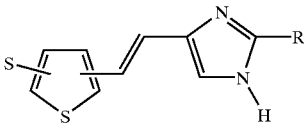

wherein the variables are dependently selected from the groups consisting of:

| 2 or 3 thienyl | X | R |
|---|---|---|
| Thien-2-yl | H | H |
| Thien-2-yl | 5-Me | H |
| Thien-2-yl | 3-Me | H |
| Thien-2-yl | 5-Cl | H |
| Thien-3-yl | H | H |
| Thien-2-yl | 4-Br | H |
| Thien-2-yl | 5-Et | H |
| Thien-2-yl | 4-Et | H |
| Thien-3-yl | 2-Et | H |
| Thien-2-yl | 3-Me | Me |

5. The compound of claim 1 having the structure:

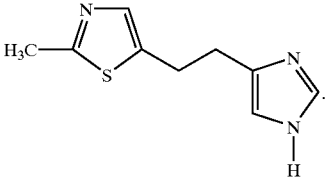

6. A method for treating a human suffering from the need for analgesia comprising the step of administering an effective amount of a compound which is a suitable α2-adrenoceptor agonist of the formula:

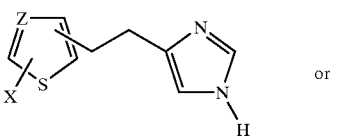

-continued

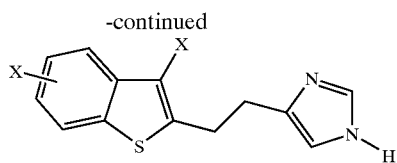

where

Z is CH or N; and

X is independently selected from the group consisting of hydrogen, $C_{1-4}$alkyl, bromine, chlorine, iodide, trifluoromethyl, $C_{1-4}$alkoxy and nitro.

7. A pharmaceutical preparation for treating a human suffering from the need for analgesia comprising a pharmaceutically acceptable carrier and an effective amount of a compound which is a suitable α2-adrenoceptor agonist of the formula:

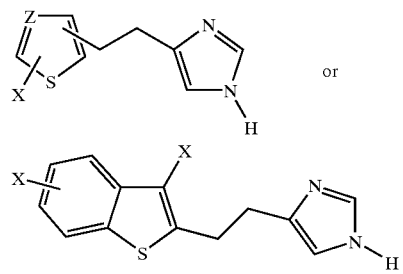

or where

Z is CH or N; and

X is independently selected from the group consisting of hydrogen, $C_{1-4}$alkyl, bromine, chlorine, iodide, trifluoromethyl, $C_{1-4}$alkoxy and nitro.

* * * * *